US006982825B2

(12) United States Patent
Sander

(10) Patent No.: US 6,982,825 B2
(45) Date of Patent: Jan. 3, 2006

(54) STEREOMICROSCOPE

(75) Inventor: Ulrich Sander, Rebstein (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 27 days.

(21) Appl. No.: 10/721,566

(22) Filed: Nov. 25, 2003

(65) Prior Publication Data

US 2004/0136059 A1    Jul. 15, 2004

(30) Foreign Application Priority Data

Nov. 29, 2002  (DE)  ................................ 102 55 961

(51) Int. Cl.
*G02B 21/22* (2006.01)
(52) U.S. Cl. ...................... 359/377; 359/431
(58) Field of Classification Search ................ 359/368, 359/372–377, 379, 380, 384, 434, 431
See application file for complete search history.

(56) References Cited

U.S. PATENT DOCUMENTS

| 4,448,498 A | * | 5/1984 | Muller et al. ................ 359/377 |
| 4,605,287 A | | 8/1986 | Lang et al. |
| 4,643,541 A | * | 2/1987 | Matsubara .................. 359/384 |
| 5,861,982 A | * | 1/1999 | Takahama et al. .......... 359/381 |
| 5,898,518 A | | 4/1999 | Biber |
| 6,081,371 A | * | 6/2000 | Shioda et al. ................ 359/372 |
| 6,356,088 B1 | * | 3/2002 | Simon et al. ................ 324/752 |
| 2001/0010592 A1 | | 8/2001 | Nakamura |
| 2003/0165012 A1 | * | 9/2003 | Straehle et al. ............. 359/431 |

FOREIGN PATENT DOCUMENTS

| DE | 43 31 635 A1 | 6/1994 |
| DE | 100 50 351 A1 | 5/2001 |

* cited by examiner

*Primary Examiner*—Mark A. Robinson
*Assistant Examiner*—Alessandro Amari
(74) *Attorney, Agent, or Firm*—Hodgson Russ LLP

(57) ABSTRACT

Stereomicroscope having an objective (6) and a zoom system (8) downstream of the objective, the optical axis (6a) of the objective forming an angle with an axis (9) of the zoom system (8), and a plurality of deflector elements (10, 12a to 12e) by means of which at least one observation beam emerging from the objective (6) can be guided into the zoom system (8), and at least one observation beam emerging from the zoom system (8) can be guided at least on to another axis (15) extending substantially parallel to the axis (9) of the zoom system (8), while on the axis (9) of the zoom system (8) and/or on the minimum of one axis (15) extending substantially parallel thereto, there is provided at least one optical element (19) for extending the beam path of the at least one observation beam along the optical axis (9) of the zoom system (8) and/or the at least one axis (15) parallel thereto.

16 Claims, 2 Drawing Sheets

STEREOMICROSCOPE

CROSS-REFERENCE TO RELATED APPLICATIONS

The present application claims priority of German patent application no. 102 55 961.9 filed Nov. 29, 2003, which is incorporated herein by reference.

BACKGROUND OF THE INVENTION

The present invention relates to stereomicroscopes of a type comprising an objective having an optical axis; a zoom system downstream of the objective having a plurality of axes, at least one of which forms an angle with the optical axis of the objective; another axis extending substantially parallel to the at least one axis of the zoom system; and a plurality of deflector elements for guiding at least one observation beam emerging from the objective into the zoom system and for guiding at least one observation beam emerging from the zoom system on to the other axis that is substantially parallel to the at least one axis of the zoom system.

Operating microscopes used in ophthalmology and neurosurgery make it possible for both a main operator and an assistant to view the same operating area.

An ophthalmological operating microscope of this kind is known for example from DE 43 31 635 C2. The operating microscope described therein has binocular tubes for the main observer and a second observer as well as a beam splitter 4 which divides the object light between the main observer and second observer. A disadvantage of this microscope is that it is relatively tall in construction as the complete magnification optical means for the main observer are arranged substantially vertically.

A stereomicroscope for use in neurosurgery for simultaneous observation by a first and second observer is known from DE 33 33 471 C2. The optical paths are divided for the first and second observer by a dividing plate, as a result of which some loss of light intensity has to be tolerated. In addition, the free working space between the objective and the object is greatly reduced.

Finally, a similar microscope is known from U.S. Pat. No. 5,898,518.

Operating microscopes of this kind have to satisfy a number of basic requirements in practice.

One requirement is that the overall height of the microscope must be kept to a minimum for ergonomic reasons. In addition, the assistant's viewer must be able to be pivoted from the right to the left hand side of the microscope (or vice versa) quickly and with no adaptation required, and neither the image quality nor the overall height should be negatively affected by any accessories (optical or optical/mechanical equipment) which are required only for certain operating techniques. Also, both the main observer and the assistant should have the opportunity to observe the so-called red reflex to the same degree.

In conventional microscopes these requirements are only partly met.

The operating microscope M840/M841 of the present Applicant, for example, ensures that the assistant and main operator actually have the same field of vision.

This is achieved by mounting the assistant's viewing device above the magnification system and using, as the magnification system, a zoom system which is made up of four identical monoscopic magnification systems. Two of the four parallel systems make up the stereoscopic magnification system for the main observer. Further systems or channels located perpendicularly on the connecting axis of these systems provide the stereoscopic magnification system for the assistant.

U.S. 2001/001 05 92 A1 discloses a microscope which can be used in neurosurgery, which comprises an objective system, a zoom system and an eyepiece system. The objective system is mounted substantially vertically, while the zoom system consisting of two individual systems or optical channels is mounted horizontally. The essential novelty of the microscope described therein is that the axis of the zoom system is located perpendicularly to the axis of the main objective. The zoom system consists of two identical magnification channels the axes of which extend parallel to each other, thereby ensuring stereoscopic viewing of an object. One disadvantage of the microscope described therein is that as a result of the use of a semi-transparent beam splitter for spatially separating an assistant's optical path from the main operator's optical path, relatively great loss of light is unavoidable. As the beam splitter of the assistant's microscope also has the illuminating optical path passing through it, reflections are formed there, which are extremely difficult to eliminate. The observing optical path passes convergently through this beam splitter and thus leads to image errors which are difficult to eliminate. In addition, this arrangement of the beam splitter allows for an astigmatism which depends on the relative orientation of the assistant's microscope to the main microscope.

BRIEF SUMMARY OF THE INVENTION

The aim of the present invention is to provide a stereomicroscope which is easy to operate and of limited height.

This aim is achieved with a stereomicroscope having at least one optical element on the plurality of axes of the zoom system and/or on the other substantially parallel axis for extending the beam path of the at least one observation beam along a direction of the corresponding axis.

Due to the measure according to the invention of providing, on the axis of the zoom system and/or the at least (minimum of) one axis extending substantially parallel thereto, at least one optical element for extending the optical path of the minimum of one observing beam along the optical axis of the zoom system or the axis parallel thereto, the performance or versatility of a stereomicroscope can easily be improved without any unfavourable ergonomic effect on the overall height of the microscope. According to the invention additional optical components may be inserted as required into the beam paths, which can be extended as desired, without affecting the overall height of the microscope. The extension of the beam paths simply leads to a horizontal lengthening of the stereomicroscope directed substantially away from the observer, which has no ergonomic disadvantages to the observer, particularly an operator, but rather results in an improved position of the centre of gravity. Moreover, by elongating or extending a beam path, it is possible to avoid vignetting or optical field cut-off effects in case additional modules or components are inserted into the beam path.

Conveniently, the minimum of one optical element for extending the optical path produces intermediate images of an object being viewed. By means of such intermediate images it is possible overall to achieve a multi-stage image of an object which is to be viewed, by means of which the beam paths (the optical beam paths and/or the mechanical beam paths) in question can easily be lengthened overall. This lengthening may be done continuously, mechanically by means of "pull-out lengthening". Lens systems used for the pull-out lengthening are arranged so that the path is lengthened mechanically without any loss of image quality. Expediently, field lenses are used in the intermediate imaging planes or close to them, for suitably directing the beams onto a subsequent optical element.

According to a particularly preferred embodiment of the stereomicroscope according to the invention, at least one optical/mechanical component, particularly a data projecting device, an inverter device, e.g. an SDI device, a laser shutter device or an optical splitter is provided on the axis of the zoom system and/or the at least one axis extending parallel thereto. Such components can now easily be integrated in a 'stereomicroscope, particularly an ophthalmological stereomicroscope or one used for neurosurgery without having an ergonomically unfavourable effect on the overall height of the microscope. In conventional ophthalmological stereomicroscopes components of this kind could often only be used by way of a compromise as their installation would have led to an ergonomically unacceptable distance between the object to be observed (and possibly operated upon) and the observation axis of the operator and would have reduced the image quality significantly. The abovementioned components are known per se, while it should be mentioned that an SDI device (stereoscopic diagonal inverter) is an optical element for looking at the back of the eye during surgery.

Appropriately, the directions of the light of the minimum of one observing beam extend along the axis of the zoom system and the axis running parallel thereto, opposite one another. With this alignment, first of all the observing beams can be guided away from the observer or operator and subsequently, after suitable deflection, may be guided back to a binocular tube comprising the observer's eyepiece.

Thus, by a suitable arrangement of the additional optical equipment on the corresponding axes the overall height of the microscope may be optimised in the direction of the optical axis of the zoom system.

According to a particularly preferred embodiment of the stereomicroscope according to the invention, the zoom system has at least three, more particularly four magnification/observation channels. With such a construction it is possible to define observation axes for a main observer or operator and an assistant in a manner which is particularly economical with light. It is also possible to provide an ophthalmological operating microscope which gives the option of stereoscopic viewing by a main operator and only monoscopic viewing by an assistant. Because the zoom system has three magnification/observation channels, spatial separation of the main operator's optical path and the assistant's optical path can be achieved in order to define the respective observation axes in a simple manner without the need to use semi-transparent beam splitters. As a result of the horizontally extending magnification or observation channels, at the same time the overall height of the microscope can be kept very small, which is extremely favourable for ergonomic reasons. It is also possible to use the third magnification channel in order to attach a documentation device, such as a camera. In the embodiment with four observation channels both the main observer and the assistant can view the object stereoscopically. The provision of four magnification channels in the zoom system constitutes a preferred embodiment of the stereomicroscope according to the invention, as a small vertical spacing between the observation axis in question and the object is achieved, both for the main operator and for the assistant, while a particularly favourable light yield is guaranteed, as mentioned above. It is also possible to provide more than four, e.g. six or eight magnification channels, or an odd number of channels, in the zoom system.

It is preferable for the axis of the objective to extend substantially vertically and for the axis of the zoom system to extend substantially horizontally. With this arrangement of the axes the stereomicroscope according to the invention can be optimised ergonomically.

According to another preferred embodiment of the stereomicroscope according to the invention a beam splitter is provided between the main objective and the zoom system. Using a beam splitter of this kind another optical path can be split from the main optical path, by means of which the object to be viewed can be observed by another assistant. In particular, it is possible for the beam splitter together with the assistant s microscope to be continuously rotatable about the optical axis of the main objective and thus be able to be used optically in any rotated position. By continuous rotation is meant here a rotation about the optical axis of the main objective which allows any desired angle of rotation about the axis to be achieved smoothly or in stages. This measure thus helps to enable the assistant's microscope to be positioned particularly easily. The assistant's microscope is expediently adapted to be separated and/or removed from the main microscope at a mechanical separation point. This measure further increases the ease of handling of the microscope as the assistant's microscope can be removed when it is not needed.

Appropriately the data projecting device is constructed so that data projection can be carried out in front of and/or behind the zoom system. This measure can ensure that projected data, such as magnification or size data, remains unaffected by concrete zoom actuation, the data being projected into the optical path behind the zoom system. If on the other hand it is necessary to compare a reference image with an image which is to be observed under the microscope, for example, the reference image is expediently projected in front of the zoom system, so that the image to be observed and the reference image can both be magnified at the same time by the zoom system.

BRIEF DESCRIPTION OF THE SEVERAL VIEWS OF THE DRAWINGS

The invention will now be described more fully with reference to the attached drawings wherein.

DETAILED DESCRIPTION OF THE INVENTION

Figure 1:
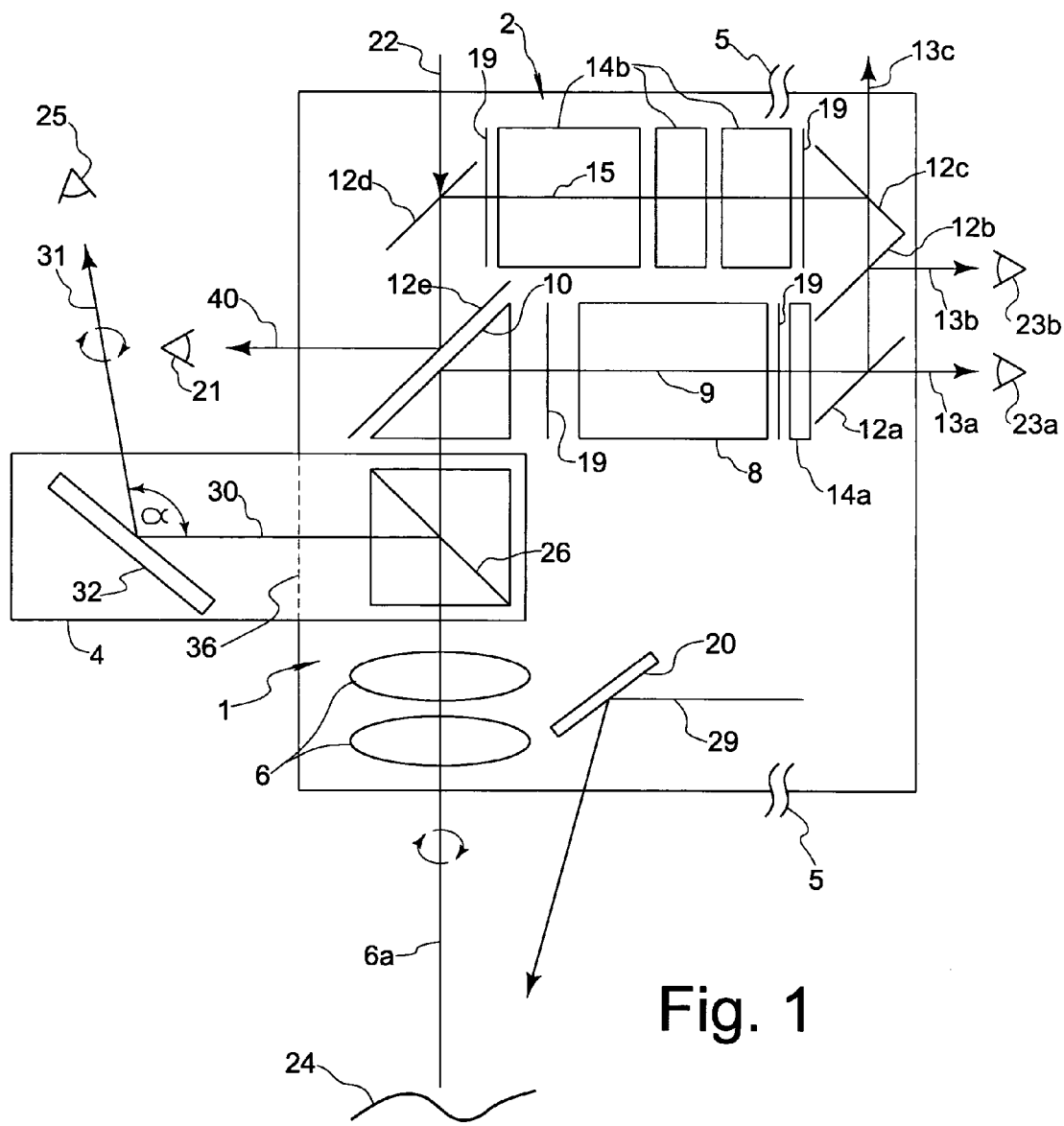
FIG. 1 is a diagrammatic side view of the overall structure of a preferred embodiment of the stereomicroscope according to the invention.

In FIG. 1 a stereomicroscope according to a preferred embodiment of the invention, shown diagrammatically, is generally designated 1. The stereomicroscope 1 comprises a main microscope 2 and an assistant's microscope 4. The stereomicroscope shown is, more particularly, an ophthalmological microscope or one used for neurosurgery.

The stereomicroscope 1 has as its essential optical components a main objective 6, a zoom system 8 and at least one binocular tube (not shown) with eyepieces. The optical axis 6a of the main objective runs vertically while the central axis 9 of the zoom system 8 runs horizontally. A first deflector element 10 is provided between the main objective 6 and the zoom system 8. Behind the zoom system 8 are provided additional deflector elements 12a to 12e and optical add-on components 14a, 14b the function or importance of which will be explained in detail hereinafter. It should be pointed out first of all that the optical add-on component 14a is constructed on the axis 9 of the zoom system 8 while the optical add-on components 14b are provided on an axis 15 extending parallel thereto, the beams emerging from the zoom system 8 passing through the optical add-on component 14a being deflected at the deflector elements 12a and 12c such that they are passed through the optical add-on components 14b along the axis 15.

On the axes 9 and 15 are provided optical elements 19 (shown diagrammatically) comprising lens systems and field lenses, by means of which the optical path of the beam extending along the axis 9 of the zoom system 8 or axis 15 can be extended. The positions of the optical elements 19 shown in FIG. 1 are merely chosen by way of example. It is also possible, for example, to form elements 19 of this kind between the three optical add-on components 14b shown.

By means of the optical elements 19, it is possible to generate a plurality of intermediate images to achieve a multi-stage image of an object 24 which is to be observed in a known way, along the axes 9, 15. By providing elements 19 of this kind the horizontal dimension of the axes 9 and 15 can be extended as desired, so that a corresponding number of optical add-on components, designated 14a, 14b in this case, as already mentioned, can be positioned as required along these axes without increasing the overall vertical height of the stereomicroscope in an ergonomically unfavourable manner. Another separation point 5 may usefully be provided where the microscope can be opened up and/or optical systems of any desired horizontal dimension may be added on.

The optical add on components 14a, 14b which may advantageously be used include, for example, a data projecting device, an inverter device, particularly an SDI device (Stereoscopic Digital Inverter), a laser shutter device or optical splitters.

Data projection may be carried out in a favourable manner using the deflector element 12d along the axis 22, as well, this deflector element 12d being semi-transparent for data projection of this kind.

The beams emerging along the axis 15 from the optical add on components 14b are deflected at the deflector element 12d perpendicularly in the downward direction and at the deflector element 12e formed below they are again deflected into the horizontal direction. A preferred observation axis for a main operator 21 is designated 40 in this case. A binocular tube with eyepieces which may be used by the main operator 21 is not specifically shown here.

It should be pointed out that the number of optical add on components 14a, 14b can be adjusted as required. If corresponding add on components are not required for specific applications, simple glass blocks may be used in their place, for example. This changeover of add on components may selectively be carried out by means of an electric motor but at the very least is done mechanically.

Reference number 20 denotes a deflector element of an illuminating device (not shown in detail). Light provided by the illuminating device along the illuminating axis 29 is directed via the deflector element 20 on to the object 24 which is to be observed.

Optionally, another beam splitter 26 may be provided between the main objective 6 and the first deflector element 10. The beam splitter 26 divides the main observation optical path along the axis 6a of the main objective 6 into two partial optical paths. A first transmitted partial optical path corresponds to the optical path discussed earlier which after deflection through the deflector element 10 extends along the axis 9 of the zoom system 8. The further partial optical path is reflected by the beam splitter 26 out of the main observation optical path as an assistant observation optical path 30. This assistant observation optical path 30 is guided by means of another deflector element 32 into an assistant binocular tube (not shown). The deflector element 32 allows tilting, thanks to its arrangement, and hence a variable-angle deflection by an amount α for the assistant 25, by means of which a variable assistant observation axis 31 can be defined.

The assistant microscope 4 may for example be capable of being separated from the main microscope at a mechanical separation point 36 (indicated by broken lines).

Another possible observation beam axis can be achieved by reflection at the deflector elements 12a, b, c. The relevant observation beam axes are designated 13a, b, c. Corresponding assistants or observers, particularly monoscopic observers or documentation devices along these observation beam axis are designated 23a, 23b.

Figure 2:
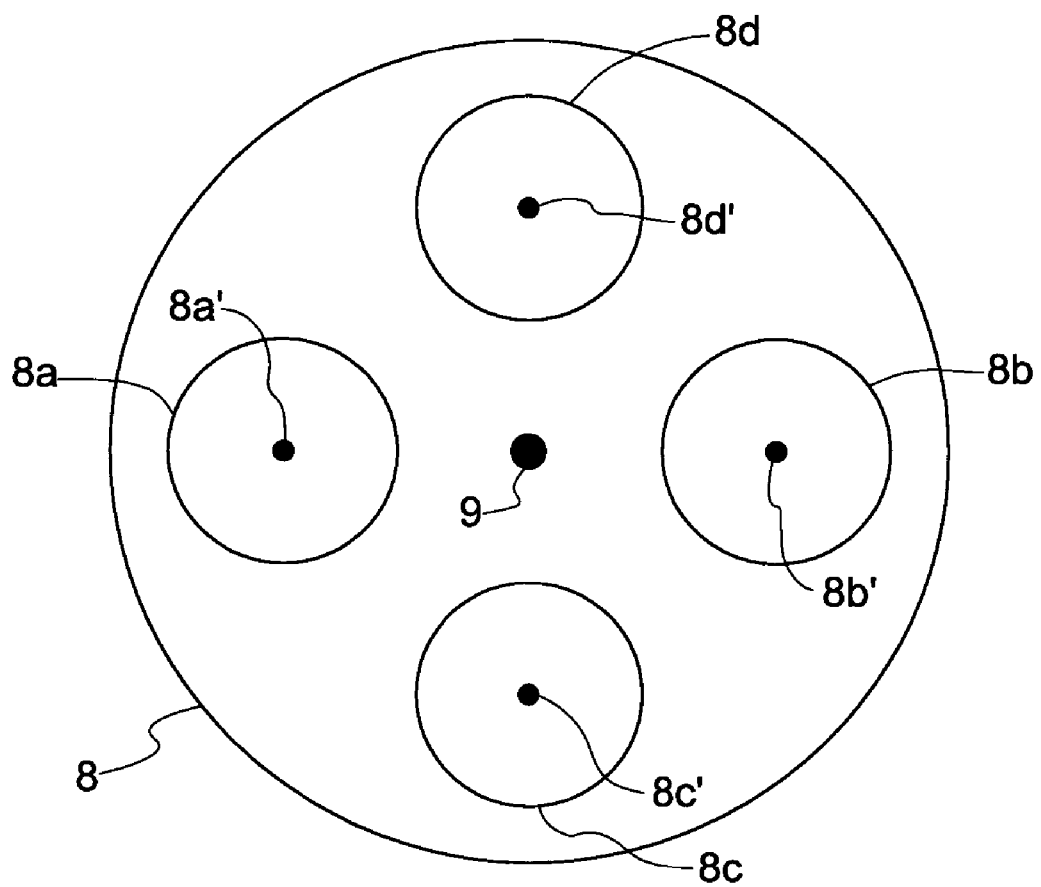
FIG. 2 is a cross sectional view of a preferred embodiment of a zoom system or which may be used according to the invention.

The zoom system used within the scope of the stereomicroscope shown expediently comprises four stereoscopic magnification/observation channels arranged in pairs, which are designated 8a to 8d in FIG. 2. The optical axes of these observation channels are designated 8a' to 8d' accordingly. The main observation channels 8a, 8b extend in a horizontal plane, i.e. substantially level with the axis 9 of the zoom system 8. These main observation channels 8a, 8b expediently form the observation channels for the main operator 21, which after the deflection described above and passing through the optical add on components 14a, 14b, can be observed by the main operator 21 along the observation axis 40.

The beams guided through the observation channels 8c, 8d extending perpendicularly one above the other are advantageously reflected out by means of the (semi-transparent) deflector element 12b along the observation axis 13. It is also possible, for example, to construct the deflector element 12a or the deflector element 12c such that only the beams passing through the main observation channels 8a, 8b are deflected, but the beams passing through the observation channels 8c, 8d are guided past the deflector element 12a. With the beams thus guided the observation channels 8a to d can also be reflected together at the deflector element 12a. Then, at the deflector element 12b, the beams 8a, 8b are selectively guided past without loss and the beams 8a, b are reflected completely into the axis 13b. The beams 8c, d in the axis 13a, b are preferably used for documentation equipment or monoscopic observer equipment as there stereo baseline runs vertically and is thus unsuitable for stereoscopic viewing without further deflection.

If the beams 8c, d are decoupled in the axis 13c, stereoscopic viewing from the plane of the drawing is possible (by the use of corresponding deflector elements). This measure allows particularly light-economical splitting of the optical paths for the main operator and monoscopic observation and/or documentation devices, as there is no need for any semi-transparent mirrors here.

LIST OF REFERENCE NUMERALS

1 Stereomicroscope
2 Main microscope
4 Assistants microscope

5 Separation point
6 Main objective
6a Axis of main objective
8 Zoom system
8a–8d Observation channels of the zoom system
8a'–8d' Axes of the zoom system
9 Axis of the zoom system
10 First deflector element
12a–12e Deflector elements
13a, b, c Observation axis
19 Optical elements
20 Deflector element
21 Main operator
22 Axis
23a, b Monoscopic observer or documentation
24 Object
25 Assistant observer
26 Beam splitter
29 Illumination axis
30 Assistant optical path
31 Observation axis assistant
32 Deflector element
36 Mechanical separation point
40 Observation axis main operator

What is claimed is:

1. A stereomicroscope comprising:
an objective (6) having an optical axis (6a);
a zoom system (8) downstream of the objective, the zoom system having a plurality of axes (9, 8a', 8b', 8c', 8d') wherein at least one of the plurality of axes of the zoom system forms an angle with the optical axis (6a) of the objective;
another axis (15) extending substantially parallel to the at least one axis of the zoom system
a plurality of deflector elements (10, 12a to 12e), by means of which at least one observation beam emerging from the objective (6) can be guided into the zoom system (8) and at least one observation beam emerging from the zoom system (8) can be guided on to the other axis (15); and
at least one optical element (19) on the plurality of axes (9, 8a', 8b', 8c', 8d') of the zoom system and/or on the other axis (15) for extending the beam path of the at least one observation beam in a direction substantially parallel to the at least one axis of the zoom system (8) and/or to the at least one axis (15) parallel thereto.

2. The stereomicroscope according to claim 1, wherein the at least one optical element (19) for extending the beam path produces intermediate images of an object (24) which is to be observed.

3. The stereomicroscope according to claim 1, further comprising at least one opto-mechanical component (14a, 14b) provided on the at least one axis of the zoom system (8) and/or on the other axis (15).

4. The stereomicroscope according to claim 3, wherein the at least one opto-mechanical component (14a, 14b) includes a data projecting device.

5. The stereomicroscope according to claim 3, wherein the at least one opto-mechanical component (14a, 14b) includes an inverter device.

6. The stereomicroscope according to claim 3, wherein the at least one opto-mechanical component (14a, 14b) includes a laser shutter device.

7. The stereomicroscope according to claim 3, wherein the at least one opto-mechanical component (14a, 14b) includes an optical splitter.

8. The stereomicroscope according to claim 3, wherein the at least one opto-mechanical component (14a, 14b) can be selectively pivoted in and out of the axis on which the at least one opto-mechanical component (14a, 14b) is provided.

9. The stereomicroscope according to claim 3, wherein the at least one opto-mechanical component (14a, 14b) can be opto-mechanically removed from the axis on which the at least one opto-mechanical component (14a, 14b) is provided.

10. The stereomicroscope according to claim 1, wherein the at least one observation beam travels in a direction along the other axis (15) that is opposite to a direction the at least one observation beam travels through the zoom system (8).

11. The stereomicroscope according to claim 1, wherein the zoom system (8) comprises at least three magnification/observation channels (8a, 8b, 8c, 8d).

12. The stereomicroscope according to claim 11, wherein the zoom system (8) comprises four magnification/observation channels (8a, 8b, 8c, 8d).

13. The stereomicroscope according to claim 1, wherein the axis (6a) of the objective (6) extends substantially vertically and the at least one axis of the zoom system (8) extends substantially horizontally.

14. The stereomicroscope according claim 1, wherein the objective (6) is arranged decentrically with respect to a first one (10) of the plurality of deflector elements (10, 12a to 12e) to receive the observation beam emerging from the objective (6).

15. The stereomicroscope according to claim 1, wherein a beam splitter (26) is mounted between the objective (6) and the zoom system (8).

16. The stereomicroscope according to claim 1, further comprising a data projecting device (22) providing information coupled into at least one observation beam path of the stereomicroscope.

* * * * *